United States Patent [19]

Haines et al.

[11] Patent Number: 4,628,063

[45] Date of Patent: Dec. 9, 1986

[54] ANTIVIRAL PHARMACEUTICAL PREPARATIONS AND METHODS FOR THEIR USE

[75] Inventors: Harold G. Haines; Caroline B. Dickens, both of Miami, Fla.

[73] Assignee: Dana P. Brigham, Miami Lakes, Fla.

[21] Appl. No.: 587,398

[22] Filed: Mar. 8, 1984

[51] Int. Cl.⁴ .................... A61K 31/16; A61K 31/195
[52] U.S. Cl. .................................. 514/626; 514/563; 514/629
[58] Field of Search ................ 424/319, 324; 514/626, 514/629

[56] References Cited

PUBLICATIONS

Chemical Abstracts 48:6521e (1954).
Chemical Abstracts 99:110755b (1983) Abstracting Rom Ro 75,309 published 3/25/82.
Chemical Abstracts, vol. 99, 1983 pp. 30cs–31cs.
Vucina et al.: Pediatria, vol. 8 (2), pp. 147–150 (1965).

*Primary Examiner*—Jerome D. Goldberg
*Attorney, Agent, or Firm*—Wegner & Bretschneider

[57] ABSTRACT

The present invention relates to a method and pharmaceutical composition for treating herpes group virus infections in mammals, and in particular, in humans, by administering an effective antiviral amount of lidocaine or a pharmaceutically acceptable salt thereof.

8 Claims, 9 Drawing Figures

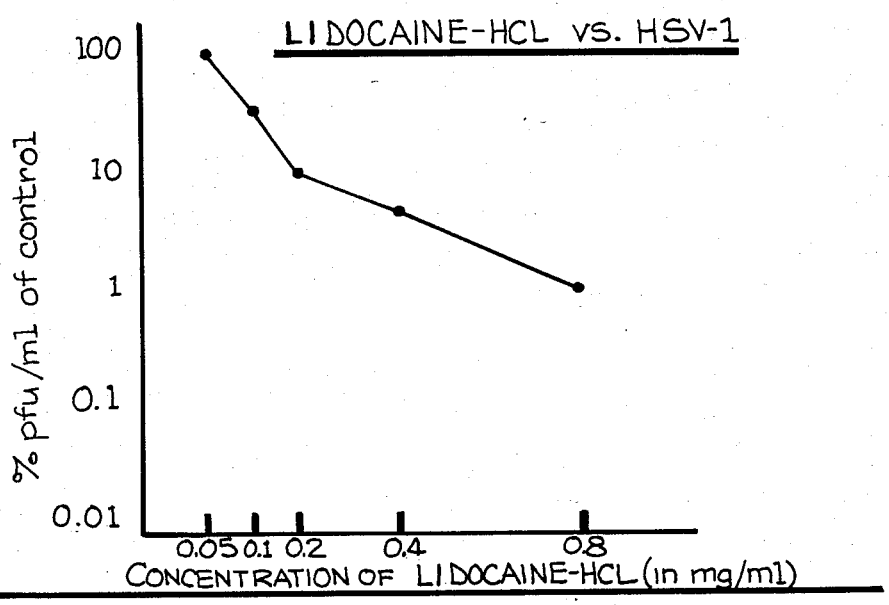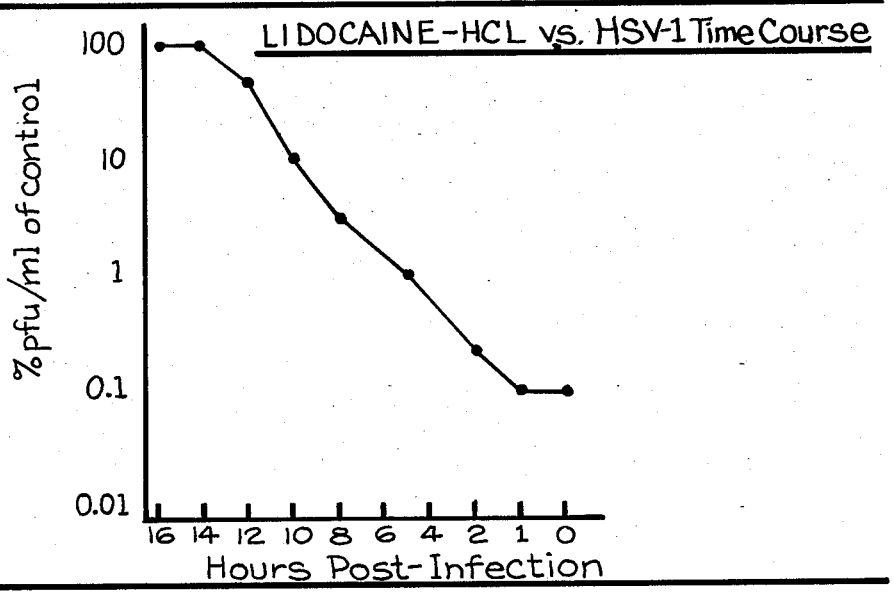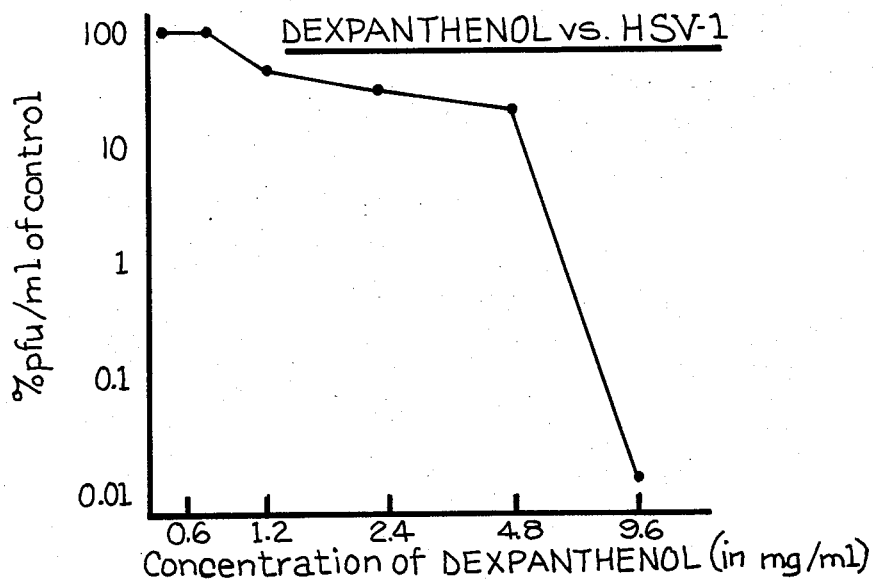

ANTIVIRAL PHARMACEUTICAL PREPARATIONS AND METHODS FOR THEIR USE

FIELD AND BACKGROUND OF THE INVENTION

This invention relates to a method and pharmaceutical composition for treating herpes group virus infections in mammals, with specific emphasis upon the treatment of herpes simplex virus infections in humans.

There are four separate herpes group viruses which infect and cause disease in humans. These are (1) herpes simplex virus 1 and 2. (HSV-1 and HSV-2); (2) cytomegalovirus (CMV); (3) varicella-zoster virus (VZ) and Epstein-Barr virus (EB). The distinct clinical entities caused by herpes simplex virus (types 1 and 2) are given in Table 1. The clinical entities caused by cytomegalovirus, varicella-zoster virus, and Epstein-Barr virus are described below.

TABLE 1

DISEASE ATTRIBUTABLE TO HERPES SIMPLEX VIRUS INFECTION

| | |
|---|---|
| Herpes Labialis | Disseminated Herpes |
| Genital Herpes | Occupational Herpes |
| Neonatal Herpes | Herpetic Gingivostomatitis |
| Herpetic Keratitis | Meningitis (Aseptic) |
| Eczema Herpeticum | Encephalitis |

Herpes viruses are a large family of viruses which contain deoxyribonucleic acid (DNA) and are surrounded by an envelope. They occur throughout nature and have been found to infect many forms of life including vertebrates and invertebrates and even fungi. One of their primary biological characteristics is to latently exist in an infected host after the primary or initial infection and in some instances, cause recurrent disease in that host due to exacerbation of the virus from the latent state. This state of latency can endure over the lifetime of an individual animal.

The first infection in humans caused by HSV-1 is generally an infection in childhood in which the virus actively infects the mucous membranes of the mouth and oral region. The clinical entity produced by this infection is called gingivostomatitis. After the initial infection runs its course, the virus becomes latent in the nerve centers (ganglia) which supply the sensory nerves to the infected area. At any point in the life of the individual, after the initial infection, due to various trigger factors which have commonly been called "stress factors," and with an unknown mechanism, the virus may reappear and cause infection in different parts of the oral or facial skin region and the resultant clinical entity is called "herpes labialis." The common names for this malady are "cold sores" or "fever blisters."

A second significant and serious disease, most often caused by HSV-2, is genital herpes (herpes progenitalis) which occurs most often as a direct result of venereal acquisition of HSV-2 from an infected individual. Once HSV-2 initially infects the genital region, it too becomes latent in the individual and can reoccur, giving rise to a series of herpes genital lesion episodes. As seen in Table 1, there are other clinical entities caused by HSV-1 and HSV-2 and these are all important in human disease.

Varicella-zoster (VZ) virus is another virus of the herpes group which causes distinct and well-known diseases in man. The first disease caused by VZ virus is chicken-pox (varicella). Generally, chicken-pox is a childhood disease, the virus being acquired through respiratory droplets spread from an infected individual to an uninfected individual. Chicken-pox is a systemic disease which produces vesicular lesions over the body of the infected person. Once the disease runs its course, the virus becomes latent in the nerves of the body and remains in a latent state throughout the life of the individual.

In some individuals, for unknown reasons, the virus may reoccur later in life and cause the clinical entity known as shingles (zoster). Shingles can be a particularly painful disease, and the pain can endure even after the lesions of the disease have cleared up (post-zoster neuralgia).

Cytomegaloviruses (CMV) are a group of viruses within the herpes virus family which are widespread in humans and numerous other mammals. A great majority of human CMV infections are subclinical; that is, the primary infection occurs with no signs or symptoms. An exception to this is a congenital infection which occasionally gives rise to cytomegalic inclusion body disease of infants. There is also a mononucleosis-like syndrome caused by this virus.

A great majority of serious cases due to CMV infection come from recurring infections in immunocompromised individuals, such as in transplant patients and in cancer patients. It has been estimated that silent CMV infections have occurred in a majority of humans by the time adulthood is reached.

Epstein-Barr (EB) virus is the causative agent of infectious mononucleosis and is another member of the herpes virus family. This virus is unique among the herpes virus group in its ability to replicate only in certain types of lymphoid cells called B-cell lymphocytes. Infections mononucleosis is a self-limited lymphoproliferative disease which generally has a benign course and only rarely is severe. There is, occasionally, deep organ involvement, such as in the liver and other potentially serious complications of this disease. To date, there is no known effective treatment for EB virus infection.

Some drugs are available for treatment of herpes group virus infections of humans. However, they do not and cannot be used to treat all herpes diseases.

In general, antiviral drugs fall into discreet categories based upon their mechanism of action. There are nucleotide analogs which interfere or halt RNA or DNA synthesis. Some compounds have the property of inhibiting maturation steps in the replication cycle of viruses. Others interfere with binding or absorption of viruses to specific hosts cells or tissues. Still others prevent the uncoating of the viruses following absorption into a cell and some restrict the spread of progeny viruses from cell to cell or from infected tissues to other sites.

The currently available anti-herpetic agents fall into the nucleic acid inhibition category and generally are purine or pyrimidine analogs. The first of these is IUDR (which is 5'-iodo 2' deoxyuridine). This compound is a halogenated pyrimidine analog and is taken up into cells, phosphorylated by viral and cellular thymidine kinases, and is incorporated into DNA instead of thymidine. DNA is replicated, but viral maturation fails because defective proteins are specified by the altered DNA. This compound is toxic to both uninfected and infected cells and as such, is less selective than the following agents. IUDR is used clinically only for herpetic keratitis lesions (eye infections) because rapid re-epithelialization of the cornea somewhat mitigates its toxicity.

The second agent somewhat useful for treating herpes infections is Ara-C (1-beta arabinofuranosylcytosine). Ara-C is an analog of cytidine and is taken up by infected and uninfected cells and is incorporated into nascent DNA following phosphorylation by viral and cell phosphorylases. It is less inhibitory to DNA synthesis than is IUDR, but it inhibits both DNA polymerase and the nucleotide diphosphate reductases. It is toxic to both infected and uninfected cells and is not used clinically because of this toxicity.

Yet another anti-herpetic compound is Ara-A (9-beta arabinofuranoxyladenine). Ara-A is deaminated to arabinosyl hypoxanthine and is phosphorylated to mono-, di-, and triphosphate derivatives which act as competitive inhibitors of DNA polymerase. The DNA polymerase that is specified by the herpes simplex virus is inhibited to a greater extent than cellular DNA polymerase and Ara-A is therefore more selective than IUDR or Ara-C. Ara-A is utilized clinically for the treatment of herpetic encephalitis.

Acyclovir (9-2-beta hydroxyethomethylguanine) is another anti-herpetic drug, a guanine analog which is converted to the active triphosphate by herpes specified thymidine kinases in infected cells. It is more readily phosphorylated in infected than in uninfected cells. The phosphorylated acylguanine inhibits viral DNA polymerase to a significantly greater degree than it does a cellular enzyme and is less toxic because of this. Acyclovir also seems to be less subject to metabolic degradation than other inhibitors. It is used clinically for primary genital herpes simplex infections and for disseminated herpes infections in immunocompromised individuals.

Phosphonoacetic acid specifically inhibits viral DNA polymerase but it is too toxic for use in humans. Trisodium phosphoformic acid inhibits herpes specified DNA polymerase and is less toxic than phosphonoacetic acid, but it is also mutagenic and is not used clinically. Interferon, extracted from human fibroblast lymphocytes or manufactured using recombinant DNA techniques is moderately effective in some reports of its use clinically but scientific studies have demonstrated that it fails to inhibit viral replication directly. Its mechanism of action is attributable to protection of uninfected cells adjacent to infected cells by an unknown protective action. Interferons are cell specific, not viral specific, in their effects and cause antiviral resistance by activating cellular genes for antiviral proteins which interact with cell surface. RNA and slow replicating viruses are the best interferon inducers and responders. Herpes simplex is a poor interferon inducer and a poor responder to interferon treatment.

A whole array of other drugs, generally nucleotide inhibitors and anti-metabolites, have been shown to be effective in their antiviral properties in cell culture and sometimes in animals; however, these drugs have not been proved to be efficacious in the treatment of HSV infections in humans. Because of their cytotoxicity, many of these drugs likely will have highly toxic properties when used to treat humans for herpes infections.

SUMMARY OF THE INVENTION

We have discovered that an amino-amide which is commonly called lidocaine (2-diethylaminoacetyl-2 6-xylidide) is an effective antiviral agent in cell culture against HSV-1 and HSV-2 and is able to treat herpes virus infections of mammals. It is particularly effective in the treatment of HSV oral and genital lesions of humans.

Furthermore, we have discovered that the addition of pantothenic acid or its alcohol and salt forms, dexpanthenol and pantothenate respectively, to lidocaine or lidocaine hydrochloride significantly enhances the antiviral activity of those drugs.

Accordingly, this invention broadly concerns a method for treating herpes group virus infections in mammals which comprises administering to the mammal an effective antiviral amount of lidocaine or a pharmaceutically acceptable salt thereof. In a further aspect, this invention provides a method of treating herpes group virus infections in humans by administering, either in topical or parenteral form, an effective antiviral amount of lidocaine or a pharmaceutically acceptable salt thereof in combination with pantothenic acid or its alcohol and salt forms.

In a still further aspect, this invention provides a pharmaceutical composition for the treatment of herpes group virus infections in mammals which comprises a combination of lidocaine or a pharmaceutically acceptable salt thereof, with pantothenic acid or its alcohol and salt forms.

Lidocaine was the first amino-amide to demonstrate clinical usefulness as a local anesthetic and many topical anesthetics that have been synthesized since the introduction of lidocaine are also amino-amides. The following compounds which are chemically related to lidocaine have been introduced into clinical practice in recent years. Prilocaine (2-propylamino-2'-propionotoluidide) (Lofgren N., Tegner C.: Acta Chem Scand 14:486, 1960); Etidocaine (2-N-ethylpropylamino-2', 6'-butyroxylide) (Adams H. J., Kronberg G. H., Takman B. H.: J Pharmacol Sci 61:1829, 1972); Mepivacaine (1-methyl-2', 6' hexahydropicolinylxyledide) (Ulfendahl H. R.: Acta Anaesthesiol Scand 1:81, 1957); and a homologue of Mepivacaine which is called Bupivicaine (1-butyl-2', 6'-hexahydropicolinylxyledide) (Henn F., Brattsand R.: Acta Anaesthesiol Scand, (Suppl) 21, p. 9, 1966).

To the extent that these and other chemically related synthetic amido-amines may function in the same manner as lidocaine and exhibit antiviral activity against herpes group viruses, such compounds are to be considered as the equivalent of lidocaine for purposes of the present invention and within the scope of the appended claims.

Chemically, lidocaine is diethylaminoacet-2, 6-xylidide and has also been designated as xylocaine or lignocaine. Lidocaine has a small excitation value and a pKa value of 7.855. These are important properties in the pharmacodynamics of lidocaine. The chemical crystallizes as a fine white needle which melts between 66–69 centigrade. It is soluble in alcohol, chloroform, oils, benzene ether, and ethyl acetate. It is only slightly soluble in water. The hydrochloride salt is highly soluble in water and melts at 128°–130° C. Solutions of lidocaine are stable and withstand boiling or autoclaving with strong acids or alkali for several hours. This is an extraordinary stability. Normally, solutions of lidocaine hydrochloride have a pH value of 6.7 to 6.9. Lidocaine is chemically stable in the laboratory; however, it can easily be biodegraded in vivo by the liver and in vitro by liver slices (Sung, C. Y. and Truant, A. P. 1954 J. Pharmacol. and Exper. Therap. 112, 432). The principal use of lidocaine in medicine has been as a local anesthetic or as an agent for peripheral nerve blocks or central nerve blocks or spinal anesthesia. It has also been used as an anti-arrhythmic. Its chemistry, clinical aspects, pharmacokinetic aspects, general pharmacological and toxological aspects have all been described and are a record of state of the art (Covino, B. G. Vassalo, H. G. The Scientific Basis of Clinical Anesthesia. Publ: Grune & Stratton, New York, New York. 1976).

Schmidt et al. (*Experentia* V. 273, pp 261-262) have shown that lidocaine is able to inhibit DNA synthesis in cell cultures, and that this inhibition is probably a result of the complexing of lidocaine with membranous structures in the cells which thereby interferes with the site of DNA synthesis. VorHees et al. (U.S. Pat. No. 4,181,725) have shown that lidocaine can be used in an ointment in a topical treatment of humans for proliferative skin diseases such as psoriasis.

Until our discovery described herein, however, lidocaine has never been described as having antiviral effect, either in cell cultures, animals, or in human beings.

Pantothenic acid, and its alcohol and salt forms, dexpanthenol and pantothenate respectively, are generally known for their vitamin activity. Pantothenic acid is commonly referred to as vitamin B5. Until our discovery, these compounds have never been described as having antiviral effect either in cell cultures, animals, or in human beings.

When lidocaine is administered in the form of a pharmaceutically acceptable salt, the salt will be a nontoxic salt, suitably an acid addition salt. An example of a pharmaceutically acceptable salt of lidocaine is lidocaine hydrochloride.

While it is possible for lidocaine or its pharmaceutically acceptable salt to be administered as the raw material, it is preferably administered in the form of a pharmaceutical formulation. The pharmaceutical formulation will comprise the active compound, together with a pharmaceutically acceptable carrier therefor. The carrier must be "acceptable" in the sense of being compatable with the other ingredients of the formulation and not deleterious to the recipient thereof. The pharmaceutical formulations may be prepared in any of the methods well known in the art of pharmacy.

When the pharmaceutical formulation is applied topically, the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the lidocaine or lidocaine salt from about 0.1 to about 10% w/v (by weight per unit volume). Pharmaceutical formulations suitable for parenteral administration includes sterile solutions or suspensions of the active compound in water or other suitable vehicle.

Lidocaine and its pharmaceutically active salts have been found to exhibit antiviral activity in cell culture and animal model systems at a concentration ranging from 0.5 mg/ml (0.05%) to 100 mg/ml (10%). The recommended intramuscular daily dosage in humans is 4.3 mg/kg. of body weight or 2.0 mg per pound of body weight. Thus, in a 150 pound man (70 kg.), the recommended daily dosage is 300 mg. This generally is injected in a single intramuscular bolus form. In topical (ointment or solution) form, a representative dosage would be the application of a 0.5 to 10% topical application (most desirably 0.5 to 4%) 3 to 4 times daily. When pantothenic acid or dexpanthenol is included in the formulation, it is preferably present at a concentration of from 5-50 mg/ml.

BRIEF DESCRIPTION OF THE DRAWINGS

These and other features and aspects of this invention will become apparent from the following specifications, and from the accompanying drawings in which—

FIGS. 1-7 are graphs which illustrate the effectiveness of the present invention against HSV-1 virus.

IDENTIFICAITON OF LIDOCAINE AS AN ANTIVIRAL SUBSTANCE

A. Cell Culture

Figure 4:
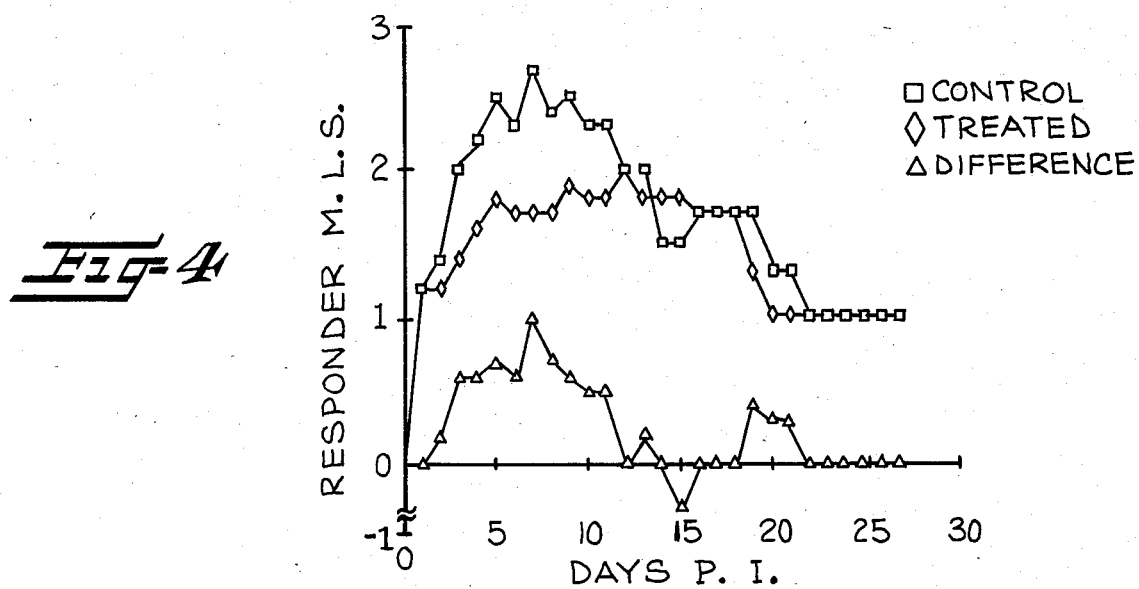

The following experiments were specifically designed to determine if lidocaine hydrochloride possesses antiviral activity against the replication of herpes simplex virus type 1 in Vero cell cultures. Harvest experiments were done in which HSV-1 infected cell cultures were post-treated with lidocaine hydrochloride at a number of concentrations. The vessels containing the cells were harvested when the cytopathic effect (CPE) in the untreated virus (negative) control cultures was 3+ to 4+ (approximately 90% of cells showing CPE). The positive control in these experiments was IUDR. The viral harvest were then plaque assayed on vero cells to determine the number of plaque forming units per millimeter (pfu/ml) produced in each test flask as compared to the controls. Table 2 shows the results of these harvest titrations and clearly points out that lidocaine hydrochloride is able to prevent the replication of herpes simplex virus type 1 in cell culture, therefore establishing it as antiviral agent. Table 2 gives the results of various concentrations of lidocaine hydrochloride from 0.4 to 1.8 mg/ml. Significant antiviral activity is seen throughout this range of concentrations. At a concentration of 2.0 mg/ml, lidocaine hydrochloride was toxic in cell cultures. FIG. 1 shows the results of decreasing concentrations of lidocaine hydrochloride, and the results shown indicate the antiviral activity of lidocaine hydrochloride is significant down to 0.1 mg/ml.

TABLE 2

| COMPONENT | *CONCEN-TRATION | HARVEST PFU/ML | LOGS VIRUS | LOG REDUCTION |
|---|---|---|---|---|
| Virus Control | — | $1.4 \times 10^6$ | 6.2 | — |
| Idoxuridine | 10 ug/ml | $7.5 \times 10^3$ | 3.9 | 2.3 |
| Lidocaine HCL | 1.8 mg/ml | 0 | 0 | >3.0 |
| Lidocaine HCL | 1.6 mg/ml | 0 | 0 | >3.0 |
| Lidocaine HCL | 1.4 mg/ml | 0 | 0 | >3.0 |
| Lidocaine HCL | 1.2 mg/ml | 0 | 0 | >3.0 |
| Lidocaine HCL | 1.0 mg/ml | 0 | 0 | >3.0 |
| Lidocaine HCL | *0.8 mg/ml | $4.5 \times 10^3$ | 3.7 | 2.5 |
| Lidocaine HCL | 0.4 mg/ml | $3.7 \times 10^4$ | 4.6 | 1.6 |

DOSE-RESPONSE OF LIDOCAINE-HCL VERSUS HSV-1 (MOI-1.0)

Because the herpes simplex virus replication cycle occurs in a well-described, orderly temporal fashion, one approach to estimating the stage of replication blocked by lidocaine hydrochloride is to perform a series of post-infection treatments with the agent, in a one-step replication cycle. In this experiment, viral cell cultures were infected with HSV-1 at a multiplicity of 3 and allowed to adsorb for one hour. The inoculum was then removed, and duplicate infected cultures were then treated at 1, 2, 4, 6, 8, 10, 12, 14 and 16 post-infection with 1.8 mg/ml of lidocaine hydrochloride in maintenance medium. At 18 hours, all cultures were washed three times with phosphate buffered saline. One milliliter of phosphate buffered saline was added back to the monolayer, and the cultures were then harvested by three cycles of freeze-thawing followed by centrifugation. The viral harvest was then titrated on viral cells, and the pfu/ml of harvest virus was calculated. The control in this experiment was a one-step multiplication cycle of untreated viral cells also infected but harvested at the same time as the treated cultures. FIG. 2 was generated from these results. From these results, it is apparent that treatment of HSV-1 infected cells with 1.8 mg/ml of lidocaine as late as 12 hours after infection is able to cause significant reduction (48%) in virus replication. When treated up to 8 hours post-infection, over 95% of virus production was inhibited. Even at 10 hours post-infection, 84% of virus production was inhibited. Because of this unusual effect, it is possible that lidocaine may act somewhat late in the herpes replication cycle unlike many effective herpes simplex antiviral drugs such as the nucleotide analogs previously described.

When dexpanthenol, in concentrations ranging from 0.6 mg/ml to 9.6 mg/ml, was tested against herpes simplex virus Type 1 in cell culture using the same assay system as described for lidocaine hydrochloride, a marked antiviral activity was seen for concentrations of dexpanthenol above 1.2 mg/ml. FIG. 3 gives the results of these experiments. In FIG. 3, it is significant that 9.6 mg/ml of dexpanthenol shows a reduction in viral titer of greater than 99.99% of the original amount of virus. Furthermore, in separate experiments, when 0.4 mg/ml of lidocaine was mixed with 0.8 mg/ml of dexpanthenol, a reduction in virus titer 50% greater than that seen with lidocaine or dexpanthenol at the same concentrations alone was observed.

These results have adequately demonstrated that lidocaine hydrochloride and dexpanthenol are effective as antiviral agents in cell culture and act by inhibiting the replication of herpes simplex virus in cell cultures.

Additional studies carried out indicate that lidocaine hydrochloride in combination with dexpanthenol in either topical or parenteral forms is effective in reducing the severity of developing herpes simplex Type 1 lesions in a hairless mouse model system when given at the time of infection of the mice or when treatment is continued for one week after infection. It is also effective in reducing the severity of developing HSV-1 lesions in hairless mice when injected at the time of initial onset of the lesions. The results of these experiments are reported below.

B. Animal Experiments

Experiment One

Figure 5:
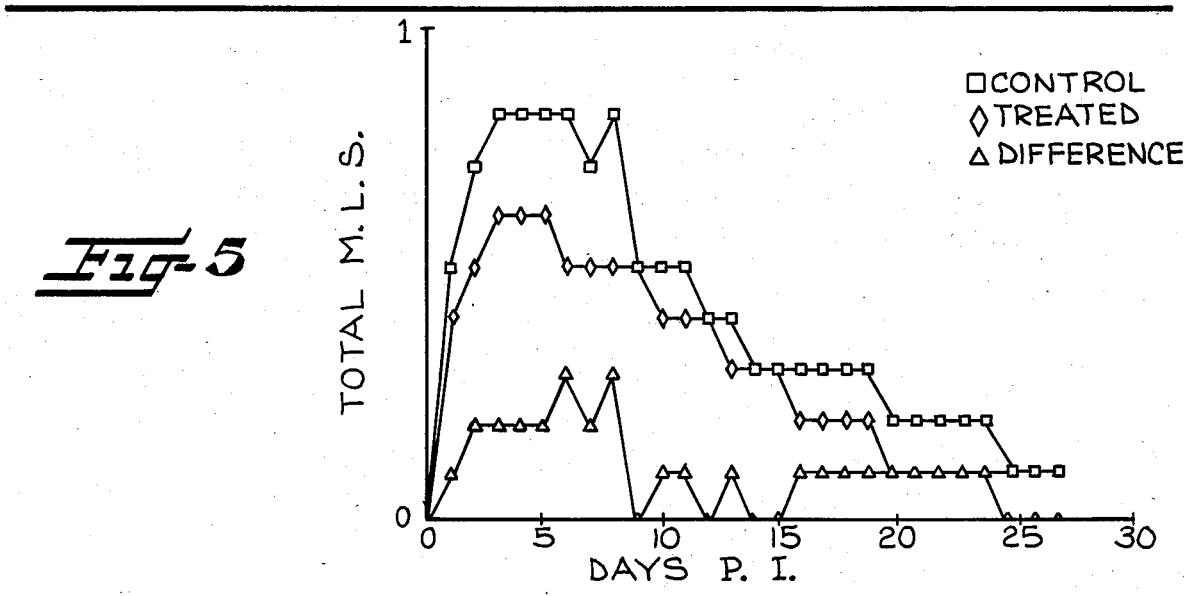
Figure 6:
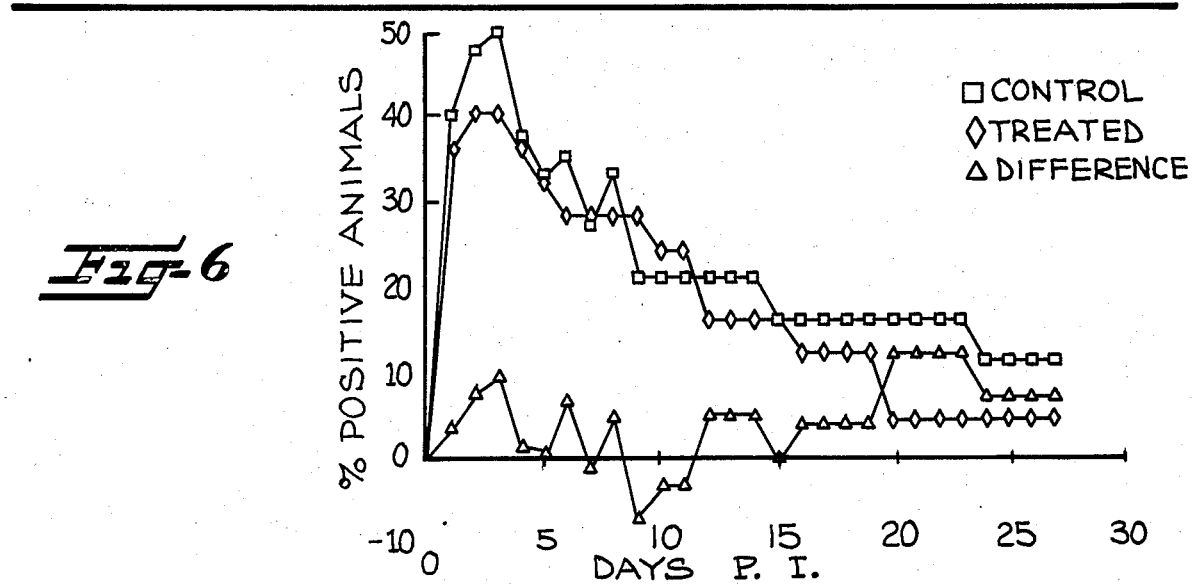

In this experiment, animals were scratch inoculated with HSV-1 and placebo (Group 1) or lidocaine hydrochloride-dexpanthenol (Group 2) ointment (lidocaine 40 mg/ml para amino-benzoic acid 5%, panthenol 50 mg/ml in a base of wheat germ oil, cetyl alcohol, petrolatum, stearyl alcohol, tween 80, water, succinic acid, and ascorbic acid added as preservative and anti-oxidant) was applied ten minutes later and one additional time on the first day. The animals were then treated daily for seven days. FIG. 4 shows the results of the responder mean lesion scores for the placebo and the treated animals. The responder mean lesion scores are defined as the cumulative lesion score of those animals which actually had lesions divided by the total number of animals with lesions. In this and every following figure, the control (placebo group) is indicated by squares and the treatment group is indicated by diamond shaped symbols. The arithmetical difference between the treatment and the control group is indicated by triangles. The results of this experiment indicate there is a significant difference ($P<0.005$) between the control animals and the prophylactically treated animals. Lidocaine hydrochloride-dexpanthenol ointment applied daily after the time of scratch inoculation prevents the development of lesions as severe as those in the control group to a significant degree. This effect is seen for the first ten days of lesion development and healing. The scores even out after approximately ten days. FIG. 5 compares the same groups of animals with respect to the total mean lesion scores. Total mean lesion score is defined as the total lesion score of animals with lesions divided by the total number of animals. This system of analysis takes into account those animals which did not develop lesions. In FIG. 5, it is seen that there is a significant difference between the treated animals and the control group at approximately the same level as seen in FIG. 4. The level of significance is $P<0.005$. This indicates that the two methods of data evaluation do not produce a difference in the outcome. FIG. 6 compares the total number of animals which developed lesions in the placebo and treatment groups and indicates that there was not a significant difference in the number of animals which developed lesions. These results indicate in this experiment that lidocaine hydrochloride-dexpanthenol ointment when applied at the time of scratch inoculation with herpes simplex virus Type 1 in hairless mice reduces the severity of developing lesions to a statistically significant degree.

Experiment Two

In this experiment, the animals were scratch inoculated with HSV-1 and cutaneous lesions were allowed to develop. The results are given in FIGS. 7 through 9. At the time of the first appearance of lesions, lidocaine hydrochloride-dexpanthenol solution was injected intramuscularly into the animals one time daily for one week. (Concentration of lidocaine hydrochloride per injection was 20 mg/ml; concentration of dexpanthenol was 30 mg/ml.) Approximately 0.1 milliliter was injected. The purpose of this group was to see if systemic lidocaine hydrochloride in combination with dexpanthenol could be used to successfully treat cutaneous HSV-1 lesions in the infected hairless mice after onset of the lesions. A placebo injectable solution was used as a control.

Figure 7:
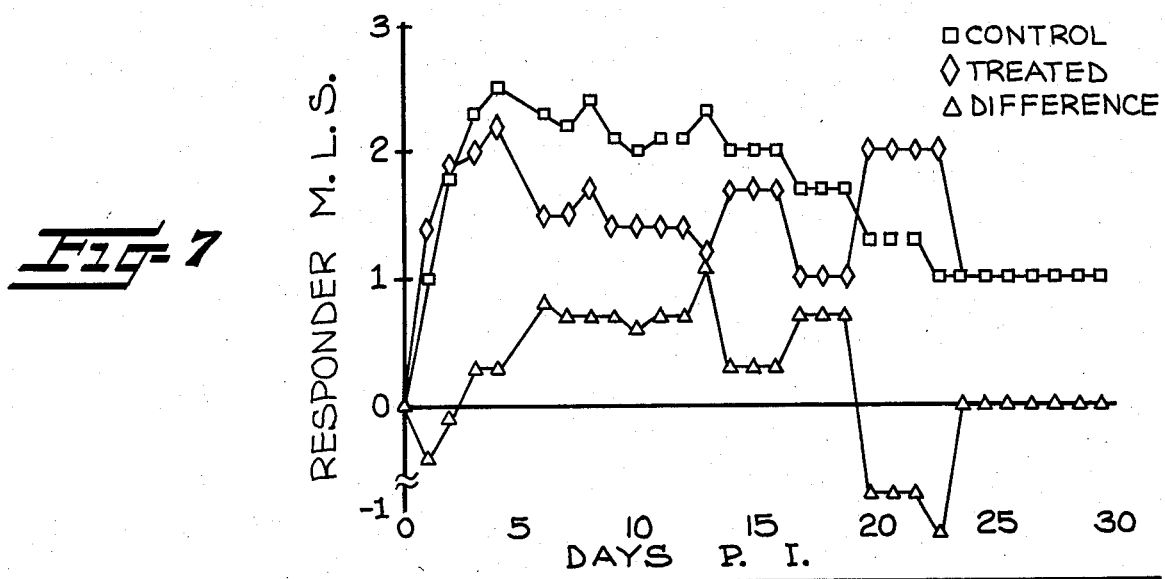

FIG. 7 indicates that there is a significant difference between the control and treated groups in the responder mean lesions score analysis ($P<0.001$).

Figure 8:
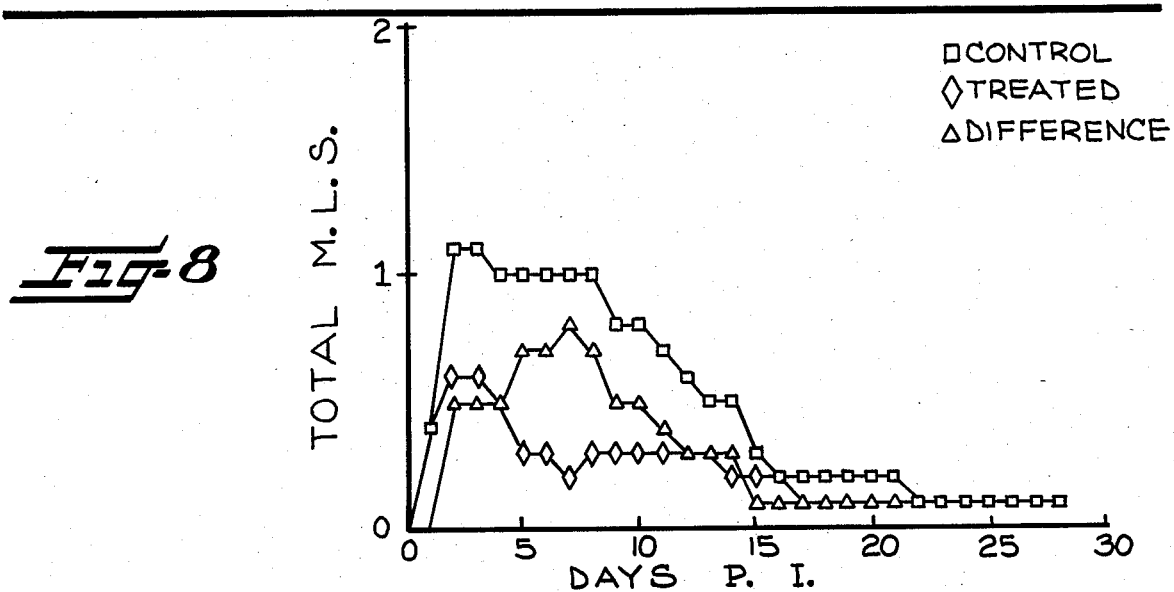

FIG. 8 similarly indicates that a difference in the total mean lesion score between the placebo and the control group.

Figure 9:
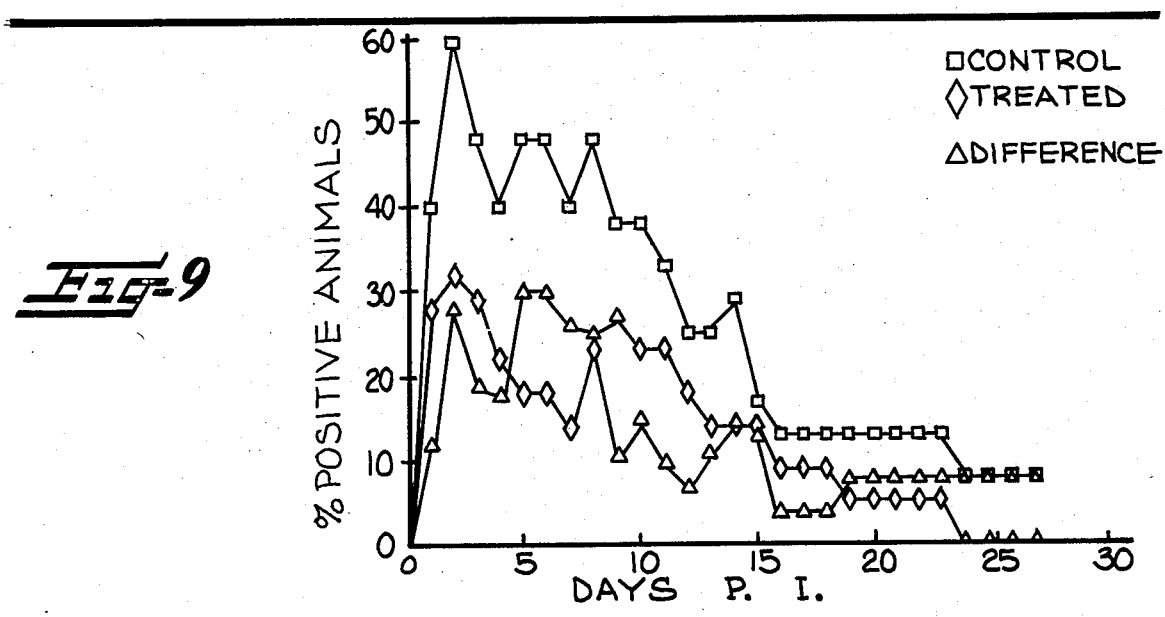

FIG. 9 indicates that the treatment group contains somewhat fewer animals that developed lesions than a control group. This is an insignificant finding since treatment was begun after lesions developed. These results indicate that injectable form lidocaine hydrochloridedexpanthenol mixture is effective in reducing the severity of herpes simplex Type 1 induced lesions in hairless mice when given at the time the first lesions initially appear in the animals.

These results indicate in a scientifically determined manner that the combination of lidocaine hydrochloride and dexpanthenol, topically applied or injected, is able to successfully treat herpes simplex virus infections in mammals.

C. Human Case Studies

EXAMPLE 1

Male Herpes Genitalis

This study comprised 14 cases, ranging in age from 16 to 50. All patients affected had had previous recurrent herpes of the genitals, with episodes recurring over periods of 1 to 6 months. The duration of genital episodes was between 10 to 14 days with intense burning before the appearance of blisters, followed by painful blisters before and after breaking, formation of scab, and remission. In this study, patients were seen before and 1 to 2 days after the appearance of blisters. They were advised to rub the affected area gently with a small amount of lidocaine hydrochloridedexpanthenol in a specially prepared ointment base 3 times a day in the morning, afternoon, and before going to bed. They were strongly advised against any sexual activity.

Results

The pre-blister itching and pain associated with the blisters was markedly reduced or disappeared 15 to 20 minutes after the first application. In 6 out of 14 patients, itching and/or pain reappeared 2 to 3 hours after the first application, but symptoms were to a lesser intensity. After the second application, 8 to 10 hours later, itching, discomfort, and pain disappeared completely and did not reappear until the complete remission of the lesions. While the disappearance of the subject's symptoms—itching, discomfort, and pain—was expected due to the anesthetic effect of lidocaine, the unexpected and beneficial results obtained were the disappearance of blisters in 2 to 3 days, together with the disappearance of symptoms of local inflammation and discomfort. All cases treated showed a definite abortion or shortening of the 7 to 10 day itching, blister, scab cycle. They all cleared up after 2 to 3 days' application of lidocaine hydrochloride ointment, regardless of the time when the treatment was instituted.

EXAMPLE 2

Anal Herpes

One patient experiencing recurrent anal herpes was treated. The patient showed definite improvement after 6 days with diminished pain. After 12 days, 75% improvement in pain and disappearance of eruptions. Previous anal herpetic episodes were lasting between 14 to 30 days with considerable pain and discomfort.

EXAMPLE 3

Herpes Zoster

Two patients with herpes zoster were treated. One patient experienced increased pain during a 24-hour period, and the treatment was discontinued after one day. The other patient with herpes zoster of the head showed definite improvement after the first treatment and consistently improved thereafter with marked lessening of pain and eruptions.

EXAMPLE 4

Herpes of the Hand

One patient was treated. Complete remission in 2 days.

EXAMPLE 5

Herpes of the face and Oral Regions

Five patients were treated. Complete remission in 2 to 5 days and diminishing of pains and symptoms of the episode.

EXAMPLE 6—Additional Case Reports

25-Year Old Male with Genital Herpes Lesions

The site of the lesion was the shaft of the penis. There was stinging and a prickly feeling at the site of the lesion; mild itching, and no burning; with a history of recurrent (6 to 7 previous episodes) lesions. This patient was treated with a combination of lidocaine hydrochloridedexpanthenol mixture in ointment form and injectable form. The lesions were healed completely in 3 days with no pain and very little discomfort, and there was no new blister formation.

26-Year Old Male

The site of the lesion was the dorsal area of the penis. Very mild lesions. There was a sensation of slight burning. Patient has had herpes episodes for 3–4 years and several episodes of gonorrhea. This individual was treated with a combination of ointment at the site of the lesions and injectable lidocaine. The lesions disappeared in 3 days. No new blisters were formed, and the pain disappeared.

34-Year Old Female

The site of the lesion was the lip, lower right side; very small blisters. This patient was presented at 5 days into the episode; no prior episodes; and no history of venereal infections. The treatment was successful and complete remission occurred in 3 days.

23-Year Old Female

Lesions just inside of the vaginal orifice. There were burning and itching sensations. These were extremely tense lesions. No history of prior episodes; no history of venereal infections. Presented with lesions of duration of about 5 days. Had tried several other presumed antiviral compounds with poor results. Upon treatment with lidocaine HCl -dexpanthenol ointment, in injectable form, the burning, pain and lesions disappeared within 4 days.

55-Year Old Female

Herpes lesions on the left hand at the base of the third and fourth fingers; red, swollen, broken blisters, oozing, with deep laceration at the base of the index finger. There was a drawing pain in the hand, itching, and burning, with pain in axillary region. The patient previously had vesicular lesions on the lips for 10 days, which disappeared. The lesions on the hand appeared following lip involvement. The lesions on the hand had been there 1 week prior to treatment. Patient had a temperature of 101° on the day prior to the visit. On the 3rd day after treatment was commenced with lidocaine hydrochloride-dexpanthenol ointment, and injectable form, the pain and swelling had subsided. All lesions disappeared within 2 weeks.

45-Year Old Female

Lesions on the introitus of the vagina; irritated, painful. This was a chronic condition, and the patient had been uncomfortable for 5 to 6 months. Treatment was commenced with lidocaine hydrochloride-dexpanthenol ointment, and injectable form, and the lesions disappeared within 3 days after a commencement of treatment.

That which is claimed is:

1. A method of treating herpes virus infections in a mammal which comprises administering to said mammal an effective antiviral amount of a mixture comprising;
    (a) lidocaine or a pharmaceutically acceptable salt thereof in a concentration of 0.5 to 10% w/v, and
    (b) pantothenol or a pharmaceutically acceptable salt thereof in a synergistically effective amount of at least 3% w/v producing an enhancement in the antiviral effect.

2. A method as in claim 1 in which the lidocaine is administered in the form of the hydrochloride salt thereof.

3. A method of treating cutaneous herpes simplex virus infections in humans which comprises topically administering to the infected areas of the human an ointment or gel containing as active ingredients;
    (a) lidocaine or a pharmaceutically acceptable salt thereof in a concentration of 0.5 to 10% w/v, and
    (b) pantothenol or a pharmaceutically acceptable salt thereof is a synergistically effective amount of at least 3% w/v producing an enhancement in the antiviral effect.

4. A method according to claim 3 wherein lidocaine is administered in the form of the hydrochloride salt thereof.

5. A pharmaceutical composition for the treatment of herpes group virus infections in a mammal which comprises an effective antiviral amount of a mixture comprising;
    (a) lidocaine or a pharmaceutically acceptable salt thereof in a concentration of 0.5 to 10% w/v, and
    (b) pantothenol or a pharmaceutically acceptable salt thereof in a synergistically effective amount of at least 3% w/v producing an enhancement in the antiviral effect.

6. A pharmaceutical composition according to claim 5 comprising lidocaine hydrochloride.

7. A pharmaceutical composition according to claim 5 in a pharmaceutically acceptable ointment base.

8. A pharmaceutical composition according to claim 5 comprising the mixture in a sterile solution.

* * * * *